(12) United States Patent
Adahan

(10) Patent No.: US 8,235,972 B2
(45) Date of Patent: Aug. 7, 2012

(54) SUCTIONING SYSTEM, METHOD AND KIT

(76) Inventor: Carmeli Adahan, Jerusalem (IL)

( * ) Notice: Subject to any disclaimer, the term of this patent is extended or adjusted under 35 U.S.C. 154(b) by 841 days.

(21) Appl. No.: 12/223,473

(22) PCT Filed: Nov. 8, 2006

(86) PCT No.: PCT/IL2006/001287
§ 371 (c)(1),
(2), (4) Date: Jul. 31, 2008

(87) PCT Pub. No.: WO2007/088530
PCT Pub. Date: Aug. 9, 2007

(65) Prior Publication Data
US 2009/0030402 A1    Jan. 29, 2009

(30) Foreign Application Priority Data
Jul. 24, 2006    (WO) .................. PCT/IL2006/000855

(51) Int. Cl.
*A61M 1/00*    (2006.01)
(52) U.S. Cl. .......... 604/540; 604/35; 604/305; 604/306; 604/307; 604/308; 604/313; 604/317; 604/318; 604/319; 604/320; 604/321; 604/322; 604/323; 604/541; 604/542; 604/543; 604/544; 604/902; 606/131
(58) Field of Classification Search ........... 604/540–544
See application file for complete search history.

(56) References Cited

U.S. PATENT DOCUMENTS

| | | |
|---|---|---|
| 599,333 A | 2/1898 | Hulse |
| 1,599,899 A | 9/1926 | Kettering et al. |
| 3,416,461 A | 12/1968 | McFarland |
| 3,516,160 A | 6/1970 | Leffler |
| 4,108,574 A | 8/1978 | Bartley et al. |
| 4,208,171 A | 6/1980 | Jonsson |
| 4,447,226 A | 5/1984 | Mayoral |
| 4,552,552 A | 11/1985 | Polaschegg et al. |
| 4,583,970 A | 4/1986 | Kirchner |
| 4,611,627 A | 9/1986 | Eidsvoog et al. |
| 4,661,093 A | 4/1987 | Beck et al. |
| 4,739,791 A | 4/1988 | Adahan |
| 4,930,997 A | 6/1990 | Bennett |
| 5,116,206 A | 5/1992 | Adahan |
| 5,370,610 A | 12/1994 | Reynolds |
| 5,419,687 A | 5/1995 | Adahan |
| 5,636,643 A | 6/1997 | Argenta et al. |
| 5,645,081 A | 7/1997 | Argenta et al. |
| 5,662,599 A | 9/1997 | Reich et al. |
| 5,776,119 A | 7/1998 | Bilbo et al. |
| 5,941,859 A | 8/1999 | Lerman |

(Continued)

FOREIGN PATENT DOCUMENTS

DE    24 01 643 A1    7/1975

(Continued)

*Primary Examiner* — Tatyana Zalukaeva
*Assistant Examiner* — Ilya Treyger
(74) *Attorney, Agent, or Firm* — Vorys, Sater, Seymour & Pease, LLP; Susanne M. Hopkins; William L. Klima

(57) ABSTRACT

A suction head in fluid communication with a pump head provides a sub-ambient working pressure to a target area, enabling drainage thereof to a waste container. The pump head is coupled non-mechanically to a pump drive. A control system for a suction system is also provided.

18 Claims, 3 Drawing Sheets

U.S. PATENT DOCUMENTS

| | | |
|---|---|---|
| 5,947,923 A | 9/1999 | Uehara et al. |
| 6,042,560 A | 3/2000 | Niederberger |
| 6,071,267 A | 6/2000 | Zamierowski |
| 6,257,847 B1 | 7/2001 | Silver et al. |
| 6,471,982 B1 | 10/2002 | Lydon et al. |
| 6,562,013 B1 | 5/2003 | Marasco, Jr. |
| 6,648,862 B2 | 11/2003 | Watson |
| 6,824,533 B2 | 11/2004 | Risk, Jr. et al. |
| 7,128,735 B2 | 10/2006 | Weston |
| 7,229,422 B2 | 6/2007 | Klobe |
| 7,255,681 B1 | 8/2007 | Silver et al. |
| 7,503,910 B2 | 3/2009 | Adahan |
| 2001/0029956 A1 | 10/2001 | Argenta et al. |
| 2002/0151826 A1 | 10/2002 | Ramey et al. |
| 2003/0014022 A1 | 1/2003 | Lockwood et al. |
| 2003/0040687 A1 | 2/2003 | Boynton et al. |
| 2003/0050594 A1 | 3/2003 | Zamierowski |
| 2003/0097100 A1 | 5/2003 | Watson |
| 2004/0015042 A1 | 1/2004 | Vincent et al. |
| 2004/0039243 A1 | 2/2004 | Bearnson et al. |
| 2004/0059284 A1 | 3/2004 | Nash et al. |
| 2004/0064132 A1 | 4/2004 | Boehringer et al. |
| 2004/0199840 A1 | 10/2004 | Takeoka et al. |
| 2005/0004534 A1 | 1/2005 | Lockwood et al. |
| 2005/0180868 A1 | 8/2005 | Miller |
| 2005/0192548 A1 | 9/2005 | Dolliver et al. |

FOREIGN PATENT DOCUMENTS

| | | |
|---|---|---|
| DE | 32 05 445 A1 | 8/1983 |
| DE | 32 05 449 C2 | 9/1983 |
| DE | 102 15 896 A1 | 10/2003 |
| EP | 0 156 211 A2 | 10/1985 |
| EP | 0865304 B1 | 7/2001 |
| GB | 2 307 180 A | 5/1997 |
| GB | 2 378 734 A | 2/2003 |
| JP | 2002035111 A | 2/2002 |
| JP | 2002541978 A | 12/2002 |
| WO | 8401904 A1 | 5/1984 |
| WO | WO 96/05873 A1 | 2/1996 |
| WO | WO 97/18007 A1 | 5/1997 |
| WO | WO 00/02016 * | 1/2000 |
| WO | WO 00/02016 A1 | 1/2000 |
| WO | 0064394 A1 | 11/2000 |
| WO | WO 03/016719 A1 | 2/2003 |
| WO | WO 03/030966 A1 | 4/2003 |
| WO | WO 03/057070 A2 | 7/2003 |

* cited by examiner

SUCTIONING SYSTEM, METHOD AND KIT

This application is a 371 application from International Application No. PCT/IL2006/001287, which claims priority from U.S. patent application Ser. No. 11/344,007, filed on Feb. 1, 2006, and International Application No. PCT/IL2006/000855, filed on Jul. 24, 2006; the content of each of these applications is hereby incorporated in its entirety.

FIELD OF THE INVENTION

This invention relates to suctioning systems and methods, and kits for use therewith. In particular, the invention relates to such systems and methods that apply negative pressure to physiological areas and the like.

BACKGROUND OF THE INVENTION

There are many medical situations in which applying suctioning to an area of the body may be beneficial, for example: applying a negative pressure to a wound or burn and/or draining the same, draining the trachea, draining fluids from organs and other parts of the body being operated on or being treated, including treatments of a dental nature. For example, negative pressure applied to a wound enhances drainage of fluids or exudate from the wound and promotes tissue growth and wound healing. This method of healing (known as "cupping") was exercised since the times of ancient Greek physicians until the 19th century.

There are also many non-medical situations in which applying suctioning to an area may also be beneficial.

A number of systems and methods have been developed for providing medical suctioning.

In WO96/05873 an apparatus is disclosed having a porous foamed pad connected by a tube to a canister. A vacuum pump is located within a housing having a recess for receiving the canister. A bacterial filter positioned over the outlet of the canister, and a vacuum pump sucks wound drainage fluids into the canister.

In WO 97/18007 a portable wound treatment apparatus is disclosed, including a housing containing a suction pump and a canister for containing fluids drawn from the wound. The housing is supported on a harness or belt worn by the patient and is connected to a porous dressing at the wound site by a catheter.

In WO 03/016719, a vacuum pump is disclosed having a drive and a disengageable pumping system connected thereto, and a two- or three-chambered canister within which solids, liquids and gases may be separated from one another.

In U.S. Pat. No. 6,648,862 the vacuum desiccator low pressure vacuum pump and trap and is transportable upon a user's person. The device includes a desiccator cartridge containing a fluid trapping agent, and the desiccator cartridge is connected to a vacuum pump member for providing a low vacuum pressure to the interior chamber of the desiccator cartridge. A single passage, one-way, gas/liquid flow pathway connects the inlet port of the desiccator cartridge to an occlusive dressing covering the wound to be drained. A control circuit includes one or more ancillary circuits for controlling operation of the device, such as: a power circuit, a moisture sensor, a timer circuit, a vacuum pressure sensor, and a pressure differential sensor.

In U.S. Pat. No. 5,645,081, a method and apparatus are disclosed, in which a negative pressure is applied to a wound sufficient in time and magnitude intended to promote tissue migration and facilitate closure of the wound.

In GB 2,307,180 (EP 0865304), a porous dressing is applied on a wound from which fluid is drawn into a canister via a catheter using portable suction pump. The pump is contained in housing and is worn on a harness or belt. Overfilling of canister is prevented by a filter contained in the canister and a pressure sensor which detects pressure reductions in tube between canister and pump which occur when drainage liquid covers the filter. A filter is placed between pump and canister, and pressure at the wound site is monitored by a conduit connected to the porous dressing.

In U.S. Pat. No. 4,739,791 a fluid collection container is disclosed, having an inlet connectable to a fluid source and an outlet connectable to a suction source. The container contains a closure member that closes the outlet port when the container is full. The closure member is integrated with a vent valve that is mounted to the container near the outlet.

In WO 03/030966, a system is disclosed for treating a patient with a wound, and comprises a bandage, a receptacle, and a vacuum source. The bandage comprises a cover to seal about the wound and to define a space above the wound in which a vacuum is to be formed. The bandage further comprises a port providing communication with the space. The receptacle is connected to the port to receive exudate from the wound and is provided to be placed below the wound. The vacuum source is spaced apart from the receptacle, is connected to the receptacle.

In WO 03/057070, a ventilated bandage system is disclosed for use with a wound. The system includes a bandage positioned adjacent to the wound to create a sealed environment around the wound. A vacuum source of the system is in communication with the bandage to create negative pressure between the bandage and the wound. The system may also include a first passageway or vent in communication with the bandage and with the surrounding atmosphere, and a second passageway in communication with the bandage and with the vacuum source.

In US 2005/192548, a wound drainage system is disclosed for draining fluid from a wound of a patient. The system includes a drain catheter, and a suction means applies suction at the drain catheter such that fluid is drawn from the wound. While drawing fluid from the wound, a controller periodically increases and decreases in an active manner the application of suction at the drain catheter.

In US 2006/0025727, a system is disclosed for treating a wound with suction. The system comprises a wound cover, a pump having an input port and an output port, the input port providing suction to the wound via the wound cover, and a reservoir coupled to the output port of the pump. The reservoir is adapted to receive effluent from the wound and the pump is said to be capable of maintaining a controlled level of suction at the wound.

SUMMARY OF THE INVENTION

Herein, the term "target volume" relates to any body, system or environment to which it is desired to apply a sub-ambient pressure to and/or to drain fluids therefrom. By way of non-limiting example, such a target volume may be biological or non-biological, and may comprise a body, system, environment, and so on, which may be contaminated with chemical and/or biological and/or other contaminants, regarding which it is beneficial to remove contaminated fluids therefrom.

Herein, the term "medical target volume" relates to any part (external or internal) of the body of a human or animal, regarding which it is desired to apply a sub-ambient pressure to and/or to drain fluids therefrom. By way of non-limiting example, such a target volume may comprise a wound/burn, the trachea, the stomach, intestines, any body cavity (including for example the intra-oral cavity, sinuses, etc.), an organ or other part of the body being operated on, including for example an incision therein, or regarding which there is bleeding or regarding which it is beneficial to remove fluids therefrom.

The term "fluid" as used herein includes liquids and/or gases, and may optionally include solids mixed in with said liquids and/or gases.

Herein the terms "upstream" and "downstream" are in relation to the general flow direction from the target area (or into the target area) towards the pump head, and beyond. Similarly, the terms "distal" and "proximal" are in relation to the general flow direction from the target area (or into the target area) to the pump head, and beyond.

According to one aspect of the invention, a vacuum system is provided for suctioning fluids from a target volume, comprising:

a suction head adapted for being in fluid communication with said target volume;

a waste container defining a collection volume for collection of materials that may be drained from said target volume; and a vacuum pump apparatus adapted for providing a predetermined working pressure in said system below external ambient pressure of an external environment with respect to said suction head, said vacuum pump apparatus comprising a powered pump drive and a pump head, in operation said vacuum pump apparatus being configured for enabling said pump drive to drive said pump head via a non-mechanical coupling arrangement, the pump head being in fluid communication with said suction head and with said waste container.

The suction head may be of any shape, size or form without limitation, typically suitable to the particular target volume that is being suctioned. For example, for external body applications in which the target volume is associated with wounds, burns and the like, the suction head may comprises an enclosure sealable to a perimeter of the wound/burn so as to define a confined volume comprising said target volume. In internal body applications, for example tracheal drainage and the like, the suction head may comprise a drain catheter or other similar arrangement having at least one lumen in fluid communication with said pump, and said inlet arrangement comprises at least one aperture adapted for providing fluid communication between said target volume and said at least one lumen.

By non-mechanical coupling is meant that a driving force is transmitted between the driving element of the pump drive and the driven element (pump) of the pump head without direct mechanical contact between the driving and driven elements.

In disclosed embodiments, the non-mechanical coupling arrangement comprises a pneumatic coupling arrangement. In other embodiments, the non-mechanical coupling may include a flowable medium, which may be solid or liquid, in the latter case the coupling being hydraulic. In yet other embodiments, the non-mechanical coupling may be based on magnetic attraction or repulsion of spaced driving and driven elements of the pump apparatus.

In disclosed embodiments, the vacuum pump apparatus comprises an actuation chamber that at least during operation of said system, is substantially air-tight and comprises a control volume of air that pneumatically couples the pump drive with the pump head, enabling said pump drive to drive said pump head.

The pump head may be releasably coupled mechanically to said pump drive, enabling the pump head to be selectively attached and detached from the pump drive. The pump head may comprise a pumping chamber and a pump member defining part of said pumping chamber, a pump inlet port and a pump outlet port, wherein said pump member is reciprocable via pneumatic coupling with said pump drive, to induce said working pressure in said vacuum system. The said pump member constitutes a fluid barrier member substantially preventing fluid communication between any one of said suction head and said waste container, and said pump drive, via said drive head. In fact, according to another aspect of the invention, a vacuum system is provided as above, wherein said pump head comprises a fluid barrier member substantially preventing fluid communication between any one of said suction head and said waste container, and said drive unit, via said drive head.

The pump member may be in fluid communication with said actuation chamber only via a first surface thereof, and the first surface of said pump member is on an outside of said pumping chamber. The pump drive may comprise a reciprocation drive for driving a reciprocating diaphragm member, said diaphragm member being in fluid communication with said actuation chamber only via a first surface thereof during operation of said system. The reciprocating diaphragm member and said pump member may be pneumatically coupled one with the other via said actuation chamber at least when said system is in operation.

The actuation chamber may comprise a first part, comprised in said pump head, and a second part, comprised in said pump drive, wherein said first part and said second part are configured for being reversibly sealably engaged with one another to define said control volume, at least when said system is in operation. The pump apparatus may comprise a coupling interface for reversibly mechanically coupling said pump head with respect to said drive unit, the pump head and the pump drive unit being separate assemblies. The pump apparatus may be configured for defining said actuation chamber responsive to said coupling interface being mechanically coupled to said pump head with respect to said drive unit. Part of said pump head may be accommodated in said waste container, wherein said pump member is facing a direction generally away from said collection volume, and wherein said pump inlet port and a pump outlet port are at least partially within said collection volume.

The pump inlet port may be in fluid communication with said suction head via a conduit, said pump outlet port may be in fluid communication with said collection volume and wherein said waste container is vented to said external ambient air. Alternatively, the pump inlet port may be in fluid communication with said suction head via said collection volume, and said pump outlet port may be vented to said external ambient air.

The vacuum system further comprise a venting arrangement adapted for providing, at least during operation of said system, substantially permanent fluid communication between said suction head and at least one of:

said external environment, such as to enable said working pressure to be maintained at the suction head while enabling a desired flow rate of ambient air into the suction head (for example at the wound enclosure or proximal to it, for embodiments where the suction head comprises a wound enclosure) via said venting arrangement; and an irrigation source, such as to enable irrigation of said target volume with a desired irrigation material.

The venting arrangement may comprise at least one bleeding orifice comprising an effective flow area compatible with providing said desired flow rate.

The pump head, waste container and suction head may be configured for being disposable.

Optionally, the target volume may be a medical target volume associated with a wound, burn or the like, and said suction head comprises an enclosure sealable to a perimeter of the wound burn or the like, respectively, so as to define a confined volume comprising said target volume.

The vacuum system may further comprise a non fluid invasive control system for monitoring and controlling said working pressure, said control system comprising at least one working parameter sensor for monitoring a working parameter of said powered pump drive and a comparator unit for comparing monitored data corresponding to said working parameter with threshold data, wherein the or each said working parameter is directly related to a magnitude of said working pressure provided by said vacuum pump.

The control system provides estimated pressure data based on monitored data corresponding to said working parameter. The system may further comprise at least one pressure sensor in fluid communication with said control volume and configured for monitoring a pressure thereof. The control system may be further adapted for comparing said estimated working pressure with said monitored pressure, and for optionally correcting said monitored data according to a difference determined between said estimated working pressure and said monitored pressure. Optionally, the control system may comprise a suitable alarm configured for being activated when a magnitude of said corrected monitored data exceeds or is below a magnitude of said threshold data. Optionally, the control system may comprise a display for displaying said corrected monitored data in any suitable manner.

Alternatively, the vacuum system may further comprise a non fluid invasive monitoring system, with respect to fluids to be sucked via said system, for monitoring said working pressure, said monitoring system comprising at least one pressure sensor in fluid communication with said control volume and configured for monitoring a pressure thereof. Optionally, the monitoring system may comprise a suitable alarm configured for being activated when a magnitude of said monitored data exceeds or is below a magnitude of said threshold data. Optionally, the monitoring system may comprise a display for displaying said monitored data in any suitable manner.

Thus, the vacuum system may comprise a controller including a control box having sensors for sensing the working parameters of the pump drive unit, and means for controlling the level of negative pressure at the target by controlling the drive working parameters, enabling the predetermined negative pressure level to be maintained, the sensors having no fluid communication with the target, and thus preventing any contamination of the sensors by target fluids.

In some embodiments, vacuum level reduction in the pump head may be achieved by slowing or stopping the pump drive.

According to another aspect of the invention, a vacuum system is provided comprising a vacuum pump adapted for providing a predetermined working pressure in said system below a reference pressure, said vacuum pump comprising a pump head operatively coupled non-mechanically to a powered pump drive unit, and further comprising a non fluid invasive control system for monitoring said working pressure, said control system comprising at least one sensor for monitoring a working parameter of said powered pump and a comparator unit for comparing monitored data corresponding to said working parameter with threshold data, wherein the or each said working parameter is directly related to a magnitude of said working pressure provided by said vacuum pump. The control system may be configured for calculating an estimated working pressure level based on monitored data corresponding to said working parameter. The said pump head may be pneumatically coupled to said powered pump drive unit via an actuation chamber comprising a control volume, further comprising at least one pressure sensor in fluid communication with said control volume and configured for monitoring a pressure thereof. The control system may be further adapted for comparing said estimated working pressure with said monitored pressure, and for optionally correcting said monitored data according to a difference determined between said estimated working pressure and said monitored pressure. Optionally, the control system may comprise a suitable alarm configured for being activated when a magnitude of said corrected monitored data exceeds or is below a magnitude of said threshold data. Optionally, the control system may comprise a display for displaying said corrected monitored data in any suitable manner. Optionally, the drive unit may comprise an electric motor, and at least one said parameter comprises any one of: motor current, motor voltage, motor power, motor rotational speed, motor torque.

According to another aspect of the invention, a vacuum system is provided, comprising a vacuum pump adapted for providing a predetermined working pressure in said system below a reference pressure, said vacuum pump comprising a pump head pneumatically coupled to a powered pump drive unit via an actuation chamber comprising a control volume, and further comprising at least one pressure sensor in fluid communication with said control volume and configured for monitoring a pressure thereof.

According to another aspect of the invention, a vacuum system is provided comprising a pump apparatus, a waste container, a bleed orifice, a control block and a pressure/vacuum monitoring means, wherein said control block is capable of controlling the working parameters of the pump apparatus, to generate user selectable pressure/vacuum level in such system. The pressure/vacuum monitoring means may provide feedback data to the control block for the purpose of determining whether the working parameters have in fact attained the desired/selectable pressure/vacuum in the system. The control block may alert the user of any such deviation.

According to another aspect of the invention, a kit is provided for use with a vacuum system for suctioning fluids from a target volume, comprising:

a vacuum pump head adapted for releasable operative coupling to a powered pump drive unit, said pump head comprising a pump inlet and a pump outlet for enabling working fluid to be pumped through the pump during operation thereof;

wherein said pump head is configured for being driven by said pump drive via a non-mechanical coupling arrangement. The non-mechanical coupling arrangement may comprise a pneumatic coupling arrangement. The pneumatic coupling arrangement may comprise an actuation chamber that is formed when said pump head is coupled with said powered pump such that at least during operation of said system, said actuation chamber is substantially air-tight and comprises a control volume of air that pneumatically couples the pump drive with the pump head, enabling said pump drive to drive said pump head. The actuation chamber may comprise a first part, comprised in said pump head, and a second part, comprised in said pump drive, wherein said first part and said second part are configured for being reversibly sealably engaged with one another to define said control volume, at least when said system is in operation.

Optionally, the kit may further comprise a waste container defining a collection volume for collection of drained materials in fluid communication with said vacuum pump head. The vacuum pump head may be attached to or integral with said waste container such that at least one of said pump inlet and said pump outlet is accommodated in said collection volume.

Optionally, the kit may further comprise a suction head having an inlet arrangement adapted for being in fluid communication with said target volume. The suction head may comprise an enclosure sealable to a perimeter of a wound so as to define a confined volume comprising said target volume, said enclosure being in fluid communication with at least one of said waste container and said pump inlet.

According to another aspect of the invention, a method is provided for indirectly controlling a working pressure generated by a vacuum pump apparatus in a vacuum system, said working pressure being below a reference pressure, said vacuum pump apparatus comprising a pump head operatively coupled non-mechanically to a powered pump drive unit, the method comprising at least monitoring a working parameter of said powered pump and comparing monitored data corresponding to said working parameter with threshold data, wherein the or each said working parameter is directly related to a magnitude of said working pressure provided by said vacuum pump. The method may further comprise calculating an estimated working pressure level based on monitored data corresponding to said working parameter. The pump head may be pneumatically coupled to said powered pump drive unit via a control volume, and may further comprise monitoring directly a pressure of said control volume. The method may further comprise comparing said estimated working pressure with said monitored pressure, and optionally correcting said monitored data according to a difference determined between said estimated working pressure and said monitored pressure. Optionally, the method may comprise the step of activating an alarm when a magnitude of said corrected monitored data exceeds or is below a magnitude of said threshold data. Optionally, the method may comprise the step of displaying said corrected monitored data in any suitable manner. The at least one said parameter may optionally comprises any one of: motor current, motor voltage, motor power, motor torque.

According to another aspect of the invention, a method is provided for indirectly monitoring a working pressure generated by a vacuum pump apparatus, said vacuum pump apparatus comprising a pump head pneumatically coupled to a powered pump drive unit via an actuation chamber comprising a control volume, and further comprising monitoring directly a pressure of said control volume.

According to some embodiments of the invention, a venting arrangement includes a bleed hole, or other orifice, which creates a predetermined pressure drop across it as external ambient air flows through the bleed holes and towards the pump. The flow level will generate the desired vacuum level across the bleed hole, which when connected to the target volume will provide such vacuum control at the target volume. When air flows through such a bleed hole, which restricts the flow, a pressure differential needs to be generated across such hole to force the flow therethrough. To increase the flow requires an increase in the pressure differential, and by changing or controlling the flow through the bleed holes (by controlling the flow through the pump), the pressure differential can be controlled to any desired level. Since one side of the bleed hole, is at ambient pressure, the generated pressure differential across such bleed hole provides the subambient pressure on the other side of such bleed hole, corresponding to a particular setting of the pump.

In some embodiments, the bleeding orifices may be used for venting the target volume via the suction head, while in other embodiments the bleeding holes may be used solely for preventing blockages and/or removing any blockages (including fluids, coagulates, exudates, etc.) in the conduits between the suction head and the pump. In yet other embodiments, the bleeding holes are used for ventilation of the target volume and for removing blockages from the conduit as well.

In some embodiments, the bleeding orifices may be used for introduction of irrigation fluids to the target or for reducing vacuum level at the target by introduction of ambient air, at the time the pump drive and pump head are slowed down.

According to other aspects of the invention, the pump head and pump drive unit are adapted for enabling quick, easy and simple manual connection and disconnection of the two components, without the need for tools.

In some embodiments, the pump drive unit may comprise first attachment means, and said pump head and/or container may comprise second attachment means, the two attachment means allowing said attaching of the pump head to the pump drive unit by a simple manipulation without tools such that the actuation chamber is automatically formed and the control volume defined. Further, the pump head and pump drive unit may be constructed so that said first and second attachment means provide detachment of said drive unit from said pump unit by a manipulation including at the most manual unfastening without tools and one detaching motion, and the same detaching motion also pneumatically disengages the reciprocal pump member from driving element of the drive member.

At least some, and preferably all of the pump head, waste container, suction head and pressure regulation system are configured for being disposable. Optionally, the pump head and waste container are reversibly lockably engaged with said pump drive unit by means of a latch arrangement.

A feature of at least some embodiments of the invention is that the pump drive unit indirectly drives the vacuum pump in a reciprocating manner that may induce flow or pressure pulsations to the wound area, which in turn may enhance wound drainage or healing. This pulsation effect may be enhanced in embodiments where the pump inlet is connected directly to the wound enclosure, rather than via a waste canister.

Another feature of at least some embodiments of the invention is that the integral unit, comprising the pump head and waste container, optionally together with the wound enclosure and conduit may be easily disconnected from the pump drive unit and disposed of after use, providing an alternative economical and medical solution to that of decontaminating pump parts of the prior art.

Yet another feature of at least some embodiments of the invention is that it can provide a generally reduced operating noise level as compared with the operation of prior art devices. For example, in the embodiments described herein, the pump head is accommodated within the waste container, which dampens any noise generated by the pump drive unit. Moreover, in embodiments where the waste container is in fluid communication with the wound enclosure via the pump head, only a small volume of air needs to be removed from the wound enclosure to achieve the required vacuum conditions. In such embodiments, the pump may operate at relatively low speed, required for relatively low flow rates, which has a corresponding low noise benefit. Noise reduction also results from having a non-mechanical coupling between the pump drive and the pump head, as mechanical couplings tend to generate noise.

By "non-fluid invasive monitoring" is meant that the said monitoring is done in such a way as to prevent any fluid communication between the fluid that is being caused to flow in the suction system, the pressure of which it is desired to determine, and the monitoring means, and thus excludes any sensors that are exposed to, and/or directly measure, the fluid pressure.

When a leak in the system reduces the load on the pump apparatus, as it is then operating at a lower vacuum level, such reduced load of the operating pump can be directly related to a leak, without having to make any direct measurement of the vacuum level at any point. Motor current could be one parameter which is monitored and is directly related to pump load/vacuum level. Accordingly, a control system monitors the motor current when the pump is operating properly and generating the proper vacuum level, such that any deviation from the recorded reference would be indicative of either excess load on the pump-occlusion or for reduced pump load-leakage.

If the vacuum pump comprises a disposable pump unit and the drive unit is detachably attachable to the pump unit, the monitoring/control system with monitoring means is preferably associated with the drive unit which is non-disposable.

BRIEF DESCRIPTION OF THE DRAWINGS

In order to understand the invention and to see how it may be carried out in practice, a number of embodiments will now be described, by way of non-limiting example only, with reference to the accompanying drawings, in which.

DETAILED DESCRIPTION OF EMBODIMENTS

Figure 1:
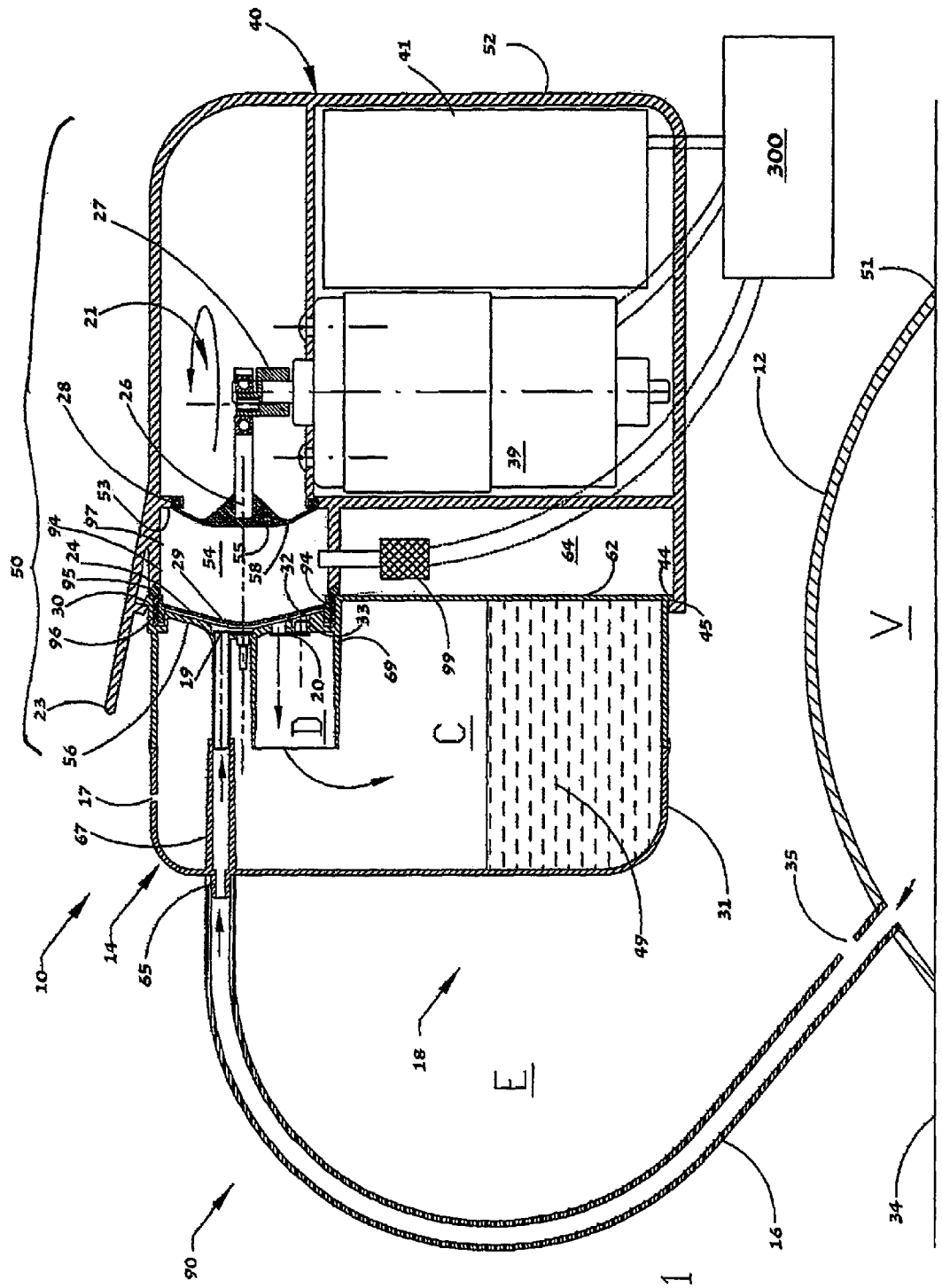
FIG. 1 is a schematic illustration in cross-sectional side view of a first embodiment of the invention.

A vacuum system for providing, i.e. applying, a sub-ambient pressure to a target volume, such as for example a medical target volume, and thus for enabling fluids to be drained therefrom according to a first embodiment of the present invention, illustrated in FIG. 1 and generally designated with the numeral 10, comprises a suction head, a vacuum pump apparatus 50, and waste canister or container 31.

The suction head has an inlet arrangement adapted for being in fluid communication with the target volume, and may be in the form of wound enclosure 12, which is associated with the target volume comprising a wound, for example. The enclosure 12 has an outer perimeter 51 that is sealable to the periphery of the wound area on the body 34. The enclosure 12 defines a confined volume V including the target volume over the exposed parts of the wound from which it is desired to remove fluids by suction, for example liquids and other flowable materials, which may include biological or non-biological materials, though at times it may be desired merely to maintain a negative pressure in the confined volume V over the wound to promote healing thereof.

The pump apparatus 50 is a powered pump, and in the illustrated embodiment comprises a reciprocating pump, which may be a diaphragm-type pump. The pump apparatus 50 comprises a pump head 14 that is releasably coupled to a pump drive unit 40 for operation therewith. The drive unit 40 comprises a housing 52 accommodating a powered drive, such as an electric motor 39, and a battery pack 41 for powering the motor. Additionally or alternatively, the motor 39 may be provided with power from an external source, such as for example an electric mains (not shown).

The system 10 may further comprise a system 300 for controlling at least one operative parameter of the motor 39, or any other drive means, to be described in greater detail hereinafter.

A reciprocating mechanism 21, comprising a crank 27 and a reciprocating head 26 coupled to a rod, is provided within the housing 52 for converting the rotary drive of the motor 39 to reciprocating motion for reciprocating head 26. The reciprocating head 26 comprises a flexible membrane or diaphragm 55 having a periphery 28 thereof suitably sealingly anchored to a frame 53 in said housing 52, such that an outer-facing surface 58 of the diaphragm 55 is exposed with respect to the housing 52. The diaphragm 55 is driven in a two-way forced reciprocation manner by means of the rod when the system 10 is in operation.

The pump head 14 comprises a pump inlet port 19 and a pump outlet port 20 comprised on a substantially rigid part 56 of the pump head 14, and a barrier member 24 that is connected at its periphery to the periphery of the rigid part 56 to define a pump working chamber 29 having a variable pump volume P. Suitable one-way valves are provided at the pump inlet port 19 and a pump outlet port 20 to ensure fluid flow in one direction through the pump head 14 from inlet port 19 to outlet port 20.

The barrier member 24 is substantially impervious to the fluids being transported through the pump head 14, and acts as a pump member, being reversibly deformable and/or movable between a first position in close proximity to the rigid part 56 defining a minimum pump volume $P_{min}$, and a second position (when maximally spaced from the rigid part 56 during operation of the system) defining a maximum pump volume $P_{max}$.

As will become clearer herein, barrier member 24 is configured for responding to changes in pressure between an inner-facing surface 33 and outer-facing surface 32 thereof such as to equalize the pressures acting on the surfaces 32 and 33 of the barrier member 24. For example, the barrier member 24 may be in the form of a highly flexible membrane or diaphragm, or a rolling diaphragm, which merely floats back and forth with the movement of media present on both sides, offering no substantial resistance to deformation and/or movement under the action of a pressure differential across its surfaces 32 and 33 in a manner such as to correspondingly change the pump volume P. Thus, under the action of a positive pressure differential between surfaces 32 and 33, the thin membrane is deformed/moved towards the rigid part 56 to assume a generally concave configuration, while under the action of a negative pressure differential, the thin membrane is sucked outwardly to assume a substantially convex configuration.

Alternatively, for example, the barrier member 24 when in the form of a rolling diaphragm, which may have a relatively rigid or non rigid central section, and a highly flexible peripheral section that is attached thereto and anchored to the periphery of the rigid part 56. Under the action of a pressure differential acting across the opposite facing surfaces 32 and 33 of the barrier member 24, the peripheral section rolls or unrolls, thereby translating the central section in the direction of the pressure differential, towards or away from the rigid part 56, respectively, depending on whether the pressure differential is positive or negative.

Thus, according to the invention, the barrier member 24 is configured for dynamically equalizing the pressures acting on either sides thereof, by translating, moving or otherwise deforming with respect to the rigid part 56, thereby correspondingly changing the magnitude of the pump volume P.

The waste container 31 comprises a suitable housing 60 defining a collection volume C adapted for collecting waste materials, particularly liquids and other flowable materials, from the wound or other target volume to which the system is coupled. Thus, the housing 60 is substantially at least one of impermeable, contamination and leak-free regarding these materials with respect to the external environment E, and may be formed as an integral item, or from several parts suitably joined together, for example.

The container 31 may be rigid or semi rigid, though in other variations of the embodiment, the container may be flexible and/or collapsible, and is in any case suitably adapted for mechanical coupling with respect to the drive unit 40. In embodiments where the container is flexible and/or collapsible, the waste container may be made from thin plastic sheet or any other suitable flexible or non-rigid material, for example, which allow it to be folded or collapsed when not full, providing the convenience of having minimal bulk and minimal inconvenience to the patient using or carrying it.

In this embodiment, the pump head 14 is joined to said waste container 31, such as to form an integral pump-head/container unit 18. However, the pump head 14 or parts thereof may be formed integrally with the waste container 31, or alternatively each component may be formed separately and joined together in any suitable manner, for example bonding, welding, fastening, and so on, to form the integral unit 18. At least a part of the pump head 14 may be accommodated in the collection volume C, in particular, the pump inlet port 19 and pump outlet port 20 are at least partially accommodated within said collection volume C, while the barrier member 24 is facing in a direction generally away from collection volume C. In other embodiments, the waste container may be separate from the pump head, and in suitable fluid communication therewith via conduits or the like.

In the first embodiment illustrated in FIG. 1, the enclosure 12 is in direct fluid communication with the pump inlet port 19 via conduit 16 that extends from the enclosure 12 and is connected to a nipple 65 on the container housing 60, and thence via a second conduit 67 that projects into the volume C from the nipple 65 and is sealingly fixed to the inlet port 19.

The outlet port 20 discharges or drains in direction shown by arrow D, via optional sleeve 69, fluids that are sucked into the pump head 14 from the enclosure 12 into the collection volume C of the container 31.

In this embodiment, the container 31 also comprises a vent 17 for venting the collection volume C to the external environment E. A suitable biological filter, hydrophobic filter or other filter (not shown) may optionally be provided at vent 17 to prevent contamination of the external environment E from the contents of the container 31.

Optionally, the waste container may contain a porous media, absorbent material, or the like, adapted to soak up said drained liquids.

The container 31, or indeed pump-head/container unit 18, comprises a coupling interface 62 that faces, and has a form that is generally complementary to, a drive unit interface 64 on the housing 52, for facilitating coupling or otherwise attaching the pump-head/container unit 18 (or container 31) with respect to the drive unit 40. The system further comprises a suitable coupling and locking mechanism, including suitable attachment arrangements on each of the pump-head/container unit 18 (or container 31) and the housing 52 (or drive unit 40), for allowing attachment or detachment one from the other, and the attachment arrangements allow attaching of the container and/or pump head to the drive unit by a simple manipulation without tools. Such attachment means may comprise, for example latch 23 engageable with tooth 30, and tab 44 engageable with slot 45, which enable coupling and decoupling of the pump-head/container unit 18 (or container 31) with respect to the drive unit 40.

The vacuum pump apparatus 50 comprises an actuation chamber 54, which, in operation of the system 10 is substantially air-tight and comprises a control volume of air that pneumatically couples the diaphragm 55 with the barrier member 24. The diaphragm 55 and the barrier member 24 are mechanically uncoupled and are spaced one from the other, in particular during operation of the system 10. The chamber 54 comprises a first part 96 that is associated with the pump head 14, and a second part 97 that is associated with the drive unit 40. The first part 96 comprises said barrier member 24 and further comprises a peripheral flange 95 that circumscribes the periphery of surface 32 and projects outwardly with respect to the pump head 14, i.e., in a direction towards the drive unit 40 when the pump head 14 is coupled therewith. Similarly, the second part 97 comprises said diaphragm 55 and further comprises a peripheral flange 94 that circumscribes the periphery of surface 58 and projects outwardly with respect to the drive unit 40, i.e., in a direction towards the pump head 14 when it is coupled with the drive unit 40. Furthermore, the first part 96 is configured to be sealingly coupled with respect to the second part 97 when the pump head 14 is coupled with the drive unit 40. In the illustrated embodiment, the flanges 94 and 95 are substantially aligned, and comprise an O-ring or other suitable sealing arrangement to enable the two flanges to be sealingly connected, when the pump head 14 is coupled with the drive unit 40. While in the illustrated embodiment the barrier member 24 and the diaphragm 55 are generally coaxially aligned, this need not be the case for other embodiments, and in fact these two components may be located wherever suitable and in whatever mutual orientation and/or spacing as may be desired, with respect to the chamber 54, so long as barrier member 24 and the diaphragm 55 are mechanically comprised in the first part 96 and second part 97, respectively.

Optionally, said flanges 94 and 95 may constitute the said coupling interface between the pump head 14 and the drive unit 40, and thus may be configured to be reversibly locked one with respect to the other and to provide sufficient mechanical integrity to the system 10 and to the chamber 54 at least during operation of the system 10.

Thus, the pump head 14 is located with respect to the container 31 at a position such that when the container 31 is mechanically coupled to the drive unit 40, the chamber 54 is formed by means of the resulting engagement of the first part 96 with the second part 97, and the barrier member 24 is pneumatically coupled with the membrane 55, at least during operation of the drive unit 40.

The chamber 54, may be in fluid communication with at least one pressure sensor or transducer 99 or any other suitable air pressure measuring device, for monitoring the pressure therein. The transducer 99 may be comprised in said drive unit 40 or remote therefrom, and is in any case operatively connected to the system 300. The transducer 99 provides feedback electrical, electronic or digitals thereto representative of the absolute or gauge pressure in the chamber 54.

In operation, as the diaphragm 55 is reciprocated in alternate opposed directions towards and away from the inside of chamber 54, cyclic pressure is applied to the control volume of air in chamber 54, which in turn pneumatically causes a corresponding displacement and/or deformation of the barrier member 24, which in turn causes the pump chamber 29 to contract and expand, thereby enabling fluids to be pumped from the enclosure 12 to the container 31. The pressure within the chamber 54 thus fluctuates in a cyclic mode, and the peak suction pressure in the chamber 54, which generally coincides with the maximum travel of the diaphragm 55 in the direction away from the chamber 54, corresponds to and is nominally equal to the maximum suction level at the pump chamber 29, since the barrier member 24 deforms/translates to equalise pressure across it. Similarly, the suction pressure at the pump chamber 29 should be substantially equal to that at the wound enclosure 12, provided that the conduit 16 is not filled with suctioned matter such as to block the conduit. Thus, the peak suction pressure at the chamber 54 should closely correspond to the peak suction pressure provided at the wound enclosure 12, and thus monitoring of the chamber pressure via transducer 99 generally provides a measure of the pressure at the enclosure 12; at the same time, the transducer 99 is effectively isolated from the pump chamber 29 via the barrier member 24.

The pump's ability to pump air and liquids, unlike conventional pumps which are typically efficient at pumping only one or the other, is enhanced by the flexibility of the barrier member 24, which allows it to yield when encountering heavy loads, such as may be present when pumping liquids.

In the illustrated embodiment, the wound enclosure 12 comprises a vent arrangement 35, that is configured for allowing a certain degree of venting of the enclosure by ambient air, when the pump 14 is in operation, such as to enable a predetermined vacuum level to be maintained at the wound enclosure 12, concurrent with providing a predetermined throughflow of ambient air into the wound enclosure 12 via the venting arrangement. The venting arrangement may comprise at least one bleeding orifice provided adjacent to the enclosure 12 as a tube orifice, or at the enclosure 12 (not shown), allowing ambient air to flow into and through suction tube 16, rendering enclosure 12 non-air tight, or vented.

The vent feature of this embodiment, unlike conventional sealed closures that are not vented, provides for quick movement of exudate entering suction tube 16, toward the vacuum pump 14, and into the waste container 31, before it dries up or coagulates and occludes the tube. This feature also provides for introduction of air at ambient pressure to the wound area of the body 34, and thus equalisation of the air pressure at the wound area with ambient pressure, whenever the vacuum pump stops pumping, allowing cyclic negative pressure application to the wound, by cycling the vacuum pump on and off alternately.

The continuous flow of ambient air through the vent arrangement 35 also assures that conduit 16 is free of liquids, to avoid creating any substantial pressure differential between vent arrangement 35 and inlet 19.

Additionally or alternatively, a conduit (not shown) may be connected to a second opening in the enclosure 12 (in addition to the first opening to which conduit 16 is coupled) and used to vent the wound enclosure to a remote location. Optionally, the free end of such a conduit may be connected to a suitable irrigation source for introducing irrigation fluids for irrigating and/or sterilizing the body area 34.

Alternatively of or additionally to the bleeding orifice 35 in the enclosure 12, a calibrated orifice or other flow restrictors may be used to provide for controlled flow of ambient air into the enclosure or into the outlet. For instance, the wound enclosure may comprise a hole plugged with open cell foam or an open pore sintered metal plug, which restrict the flow, but are not susceptible to plugging, as small dust particles will generally not plug a porous material, unlike a small orifice.

The pump unit 14 and the drive unit 40 may be calibrated such as to create a performance table or the like, which provides a relationship between operational parameters of the drive unit 40 with respect to negative pressure generated by the pump unit 14. This may be further refined, taking into account a range of effective orifice size, or other parameter that is related to the amount of ventilation provided by the venting arrangement 35. Thus, once calibrated, whenever a particular negative pressure is required at the wound enclosure 12, for a given venting arrangement ventilation, it may be assumed that this will be provided via a particular setting of the pump unit 14, and thus a corresponding setting of the drive unit 40, obtained from the aforesaid tabulated performance values.

Thus, once set, the system 10 effectively provides a desired or threshold vacuum level at the wound enclosure 12, which is remote from the pump head 14, and these conditions may be substantially maintained via an open-loop type control using the system 300. According to the invention, control of the vacuum level at the wound enclosure 12 may be further enhanced by using measured pressure levels in the actuation chamber 54 and adjusting the vacuum generated by the pump head 14 to compensate for changes thereof via a closed loop type control by means of system 300, as will become clearer herein.

According to an aspect of the invention, a system 300 and corresponding method are provided for monitoring and/or controlling variations in the sub-ambient pressure level generated by the pump apparatus, i.e., without the need for directly measuring air pressure at any point between the wound enclosure and the pump chamber 29, minimizing risk of contamination to or from the fluid being pumped therethrough. The system 300 allows for monitoring of the vacuum system of the invention for leaks and/or blockages therein in a non-invasive manner in terms of the pump unit 14 or any of the fluid paths upstream or downstream thereof, and further provides the option of controlling the operation of the drive unit 40 of the vacuum system to compensate for the leakage and/or blockage.

Thus, the drive unit 40 according to the illustrated embodiment comprises said system 300, which includes a control block with control circuits such as duty cycle controller, which turns the motor 39 on and off alternately, a motor voltage and current monitoring and controller, which controls the negative pressure level produced by the pump unit 14, by controlling the voltage and current which drive motor 39. At any given voltage which drives motor 39, the current draw of the motor is directly related to the negative pressure generated by the pump 14. Accordingly, monitoring of the current which the motor 39 draws provides indirect monitoring of the negative pressure generated by pump 14.

For example, if the motor 39 is a direct current electric motor, a sensor, such as for example an amp-meter, may measure or otherwise sense the electric current driving the motor. Since the direct current motor output torque is directly related to the current driving the motor, and since the motor output torque is directly related to the negative pressure the pump 14 produces, monitoring the motor current and controlling this current to the motor, provide for monitoring and controlling, respectively, the negative pressure produced by the vacuum pump.

Motor current monitoring is only one method for indirect negative pressure monitoring and controlling. Alternatively or additionally, the motor parameter being monitored may be the torque and/or speed of the motor, which in turn are also related to the negative pressure generated by the pump. Thus, a constant torque level or rpm may be provided by adjusting the level of the torque clutch accordingly, and/or, a torque sensor may be provided, operatively connected to an alarm, to alert the user when the torque level or rpm (and thus the negative pressure at the wound enclosure 12) drops below a predetermined value.

A similar function of negative pressure control may be accomplished by an adjustable torque limiting clutch placed between the motor output shaft and the crank 27. When the desired pre-set vacuum level is reached, the clutch will start slipping and prevent any excess motor torque from generating excess negative pressure at the target volume.

The indirect pressure measurements determined in this manner may be further refined, or indeed replaced with, direct pressure measurements at the chamber 54, obtained using transducer 99. The pressure measurements obtained via the transducer 99 are fed to the control system 300, which determines whether the working parameters driving pump head 14 are in fact producing the vacuum or pressure level anticipated by the pre-set behavior tables of the system allowing system 300 to compensate for any such deviation as well as inform/alarm the user of the existence of such deviation. For instance, if a leak develops between enclosure 12 and body 34, it would effectively increase the area available for venting, and change the working parameters of the system.

The control block of system 300 may comprise a negative pressure comparator, which compares the desired or threshold set negative pressure level to be obtained by pump 14, and the actual monitored negative pressure level as obtained indirectly from the motor voltage and current monitoring and control unit, and/or the actual monitored negative pressure level as obtained directly from the transducer 99. The comparator can activate an audible alarm whenever pump head 14 fails to reach the desired pre-set negative pressure level. Optionally, the control block may comprise a display for displaying, for example digitally, or graphically as a function of time, the vacuum level at the target volume, as derived from the drive unit parameter that is being monitored. Further optionally, where it is desired to adjust the working parameters of the drive unit 40 to control the pressure output of the pump head 14, the variation between the indirectly and directly monitored pressure (where this may occur) may be used to further adjust the working parameters of the drive unit 40 such as to enable the pump head 14 to provide a working pressure that will more closely match the desired threshold value.

The components of the control block may comprise discrete electronic components operatively interconnected to operate as described herein; alternatively, control block may comprise a suitable microprocessor unit, programmed with suitable software, and operatively coupled to the to the drive unit.

Thus, while the system 300 internally generates pressure-related data indirectly, the transducer 99 supplements thus data by providing directly obtained pressure data, none of the data having been obtained via invasive measurements of the flow path between the target volume and the pump head.

The threshold level of pressure at the target volume may be a value set by the user or by the manufacturer of the system 10. For example, the system 10 may comprise various discrete (or continuously variable) power settings for the motor 39, each of which corresponds to a particular negative pressure level at the target volume. Monitored data from the transducer 99 may be compared with the threshold level for the purpose of detecting deviations in the performance of the system 10.

The integral unit 18 comprising container 31 and valve head 14 may be provided as a kit 90, which may also comprise conduit 16, enclosure 12, optionally already connected to the unit 18. Alternatively the conduit 16 and enclosure 12, may be provided separately. The kit 90 typically also comprises a sterile bag or other packaging (not shown) that is removed before use, and after a single or one-time use it is disposed of, typically in a contamination-free manner. Thus, the unit 18 may be made from relatively inexpensive materials, compared with, for example, the manufacturing costs of the drive unit 40, and in any case may also be made from medically compatible materials, including suitable plastics and so on.

Thus, according to one aspect of the invention, the system comprises a disposable part, including integral unit 18 conduit 16 and enclosure 12, and a reusable part, including the pump drive unit 40.

The system 10 according to the first embodiment may be operated as follows. Unit 18, interconnected with the conduit 16 and enclosure 12, is mounted to drive unit 40, such that the first part 96 is sealingly engaged with the second part 97 to form sealed chamber 54, and locked together via latch 23. The enclosure 12 is placed over the wound site so as to cover the same, and the periphery 51 sealingly abutting the body 34, for example with the aid of bandages, dressings, adhesive tape, and so on. The drive unit 40 is switched on, and as the motor 39 is activated, the crank turns, reciprocating the rod and reciprocating head 26, causing the barrier member 24 to reciprocate by virtue of its pneumatic coupling with diaphragm 55 via the control volume of air in the chamber 54, and thus alternately increase and decreased the pump volume P. Thus, as the pump head 14 begins to operate, air and fluids exuded from the wound are sucked out of the contained volume V, providing a negative pressure threat and creating a partial vacuum. Fluids and other exudate materials in the wound are drawn and carried through the conduit 12 and conduit 67 directly to the inlet port 19, through the pump working chamber 29 (which is at a below-ambient, or negative, pressure when operating), and out of the outlet port 20 to the container volume C via discharge sleeve 69. As barrier member 24 reciprocates, it may induce partial cyclic flow within the conduit 16 as the air pulsates, particularly where the connection between the pump head 14 and the enclosure 12 is short, and this may cause the pressure in the enclosure 12, and thus the pressure to the wound area on the body 34 to pulsate accordingly, i.e., to fluctuate to some degree, enhancing drainage of exudates from the wound and/or enhancing the healing process by massaging this area. As exudates fills the collection volume C, air is displaced out of this volume via vent 17. If conduit 16 becomes blocked, there is more resistance to the barrier member 24 being pulled towards the chamber 54 during a suction stroke of the diaphragm 55, which in turn lowers the suction pressure monitored by the transducer 99. The control system 300 may be programmed to counter this by increasing the action of the pump head 14 to increase the suction provided by the pump apparatus 50 until the blockage is dislodged and displaced to the waste container. This monitoring also allows leaks to be identified in the system, as there is a loss of vacuum.

If the container volume C of container 31 reaches full capacity, for example the collected materials or exudates 49 reaching the level of the outlet port 20 or any other suitable level, the unit 18, conduit 16, and enclosure 12 may be disconnected from the drive unit 40 and disposed of, in a similar manner to an end of treatment scenario, as described below, and a new unit 18, conduit 16, and enclosure 12 used with the drive unit 40 to continue treatment, the pump unit having been switched off while the switching of disposable components is taking place. Alternatively, it is possible to remove and dispose of the unit 18, optionally including conduit 16, and to replace just these items to continue treatment. In such a case, patient discomfort is reduced, as the wound site is not disturbed. In other situations it may be necessary to change or replace the wound enclosure 12 while leaving the conduit 16 and/or the unit 18 in place. Thus, sometimes a kit comprising the range of items including unit 18, conduit 16, and enclosure 12 is useful, while at other times a variety of kits comprising just unit 18, or unit 18 and conduit 16, or conduit 16, or conduit 16 and enclosure 12, or enclosure 12 may also be useful.

After the completion of the suction treatment, the drive unit 40 may be switched off, and the unit 18 is unlatched from the drive unit 40, automatically disassembling the chamber 54, pneumatically disengaging the barrier member 24 from the membrane 55, and the wound enclosure is removed from the patient. The unit 18, conduit 16, and enclosure 12 are then disposed of.

Thus, once set, the system 10 effectively provides a desired vacuum level at the wound enclosure 12, which may be remote from the pump head 14, and these conditions may be substantially maintained by indirectly monitoring the vacuum level at the wound enclosure 12 and adjusting the vacuum generated by the pump head 14 to compensate for changes thereof via a closed loop type control system. The waste matter from the wound enclosure is thus suctioned to the container in a monitored and controlled manner, without contaminating the drive unit, which is regarded as a non-disposable part of the system 10. A new disposable portion, comprising a kit 90, may be immediately coupled to the drive unit 40, for immediate re-use of the system 10.

It is clear that the present invention alleviates the need for cleaning or disinfecting any portion of drive unit after use, or providing protective means, such as filters, to keep contaminants from reaching the costly drive.

Figure 2:
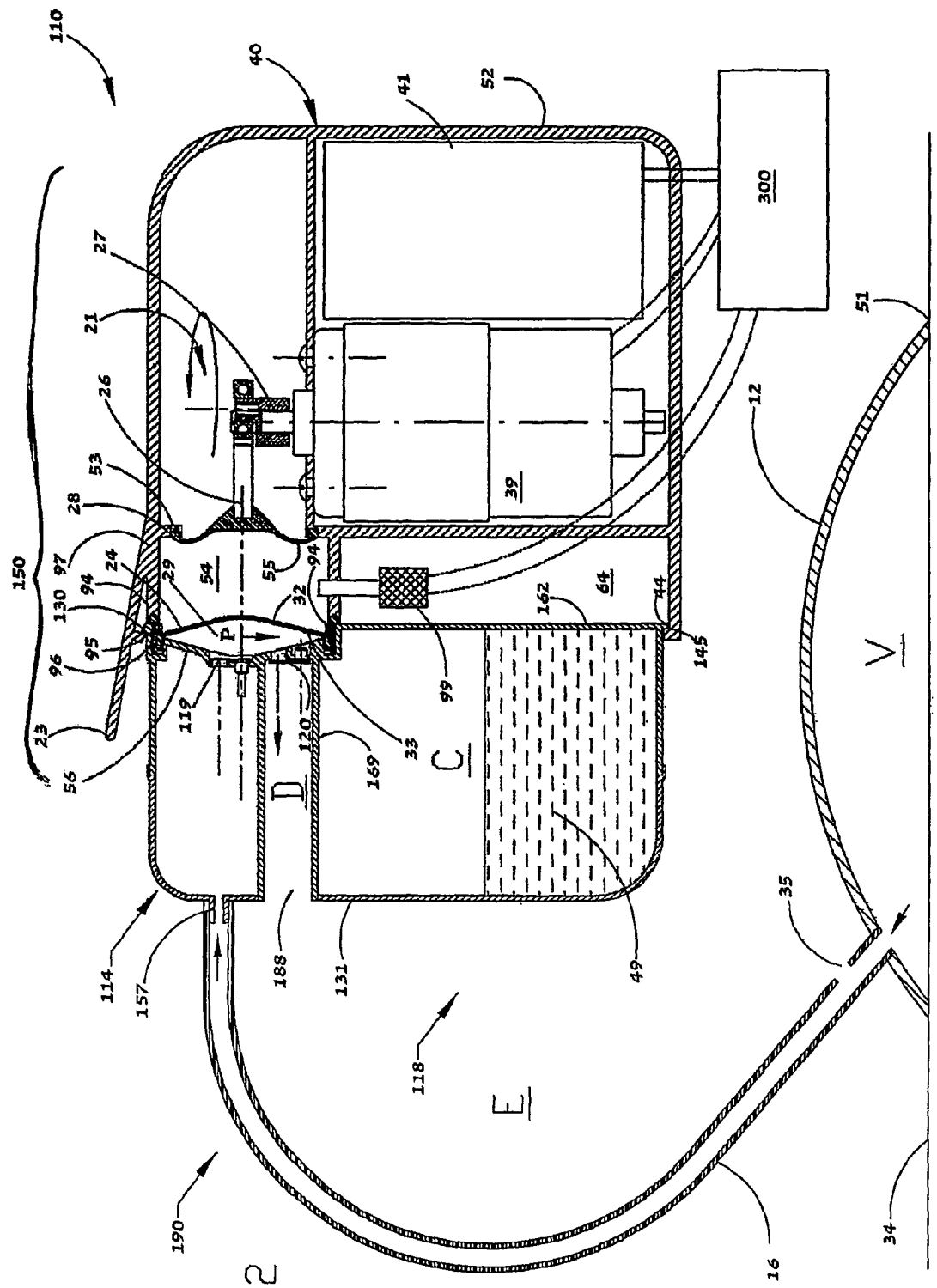
FIG. 2 is a schematic illustration in cross-sectional side view of a second embodiment of the invention.

A vacuum system for draining an open wound according to a second embodiment of the present invention, illustrated in FIG. 2, comprises the elements and features of the first embodiment, with some differences as described below, mutatis mutandis. Thus, the system 110 according to the second embodiment also comprises a wound enclosure 12, and a vacuum pump apparatus 150, and waste canister or container 131.

The wound enclosure 12 is similar to that of the first embodiment, mutatis mutandis, having an outer perimeter 51 that is sealable to the periphery of the wound area on the body 34 and defining a confined volume V, and comprising orifice 35.

The vacuum pump apparatus 150 is similar to that of the first embodiment, mutatis mutandis, and thus comprises a pump head 114 that is releasably coupled to a pump drive unit 40 for operation therewith, the drive unit 40 being substantially identical to that of the first embodiment and comprising the elements and features, as described herein for the first embodiment.

Similarly, the pump head 114 comprises rigid part 56 having a pump inlet port 19 and a pump outlet port 20 with suitable one-way valves, and a barrier member 24, defining a pump working chamber 29 having a variable pump volume P, together with a first part 96 of the chamber 54, similar to the corresponding components described for the first embodiment, mutatis mutandis.

The waste container 131 is similar to that of the first embodiment, mutatis mutandis, and thus comprises housing 160 defining collection volume C, interface 162, coupling/decoupling and locking mechanisms, for example such as latch 23 and tooth 130, tab 44 and slot 145, similar to the corresponding components described for the first embodiment, mutatis mutandis.

In the second embodiment, the pump head 114 is also joined to said waste container 131, to form an integral unit 118 similar to the corresponding components described for the first embodiment, mutatis mutandis, and the pump inlet port 19 and pump outlet port 20 are at least partially accommodated within said collection volume C, while the barrier member 24 is facing in a direction generally away therefrom.

In contrast with the first embodiment, in the second embodiment the enclosure 12 is in direct fluid communication, via conduit 16 and waste container inlet port defined by nipple 157, with the container 131, rather than the pump inlet port 19, which in this embodiment opens to the collection volume C. Thus, exudates from the wound are directly discharged to the collection volume C. The outlet port 120, on the other hand, discharges to sleeve 169 that extends to the outside of the housing 160 via exit port 188. A suitable filter (not shown) may optionally be provided between the outlet port 20 and exit port 188 to prevent contamination of ambient air. The outlet port 20 is thus vented to the external ambient environment E, and thus there is no direct communication between the container volume C and the outlet port 120. Optionally, a baffle plate arrangement (not shown) may be provided downstream of the outlet port 20, which may be useful in attenuating noise with respect to the external environment.

The container 131 does not comprise a vent corresponding to vent 17 of the first embodiment for venting the collection volume C.

As with the first embodiment, mutatis mutandis, the integral unit 118 may be provided as a kit 190, which may also optionally comprise conduit 116, and enclosure 12, optionally already connected to the unit 118, or alternatively, conduit 16, and enclosure 112, may be provided separately to the integral unit 118.

As with the first embodiment, mutatis mutandis, when the pump unit 114 and drive unit 40 are mechanically coupled, the first part 96 sealingly engages with the second part 97 to form chamber 54, pneumatically coupling the membrane 55 to the barrier member 24, and the second embodiment may be operated and controlled in a similar manner to that described for the first embodiment, mutatis mutandis.

In other embodiments of the invention, the suction head may comprise instead of the wound enclosure, a drain catheter or the like, for example, for applying a predetermined vacuum to a medical target area, such as for example the intra-oral cavity, trachea, an organ of the body being operated on, and so on, or indeed to a non-medical target area. Such a drain catheter may comprise at least one lumen in fluid communication with the pump, and the inlet arrangement may comprise at least one aperture adapted for providing fluid communication between the target volume and the at least one lumen.

Figure 3:
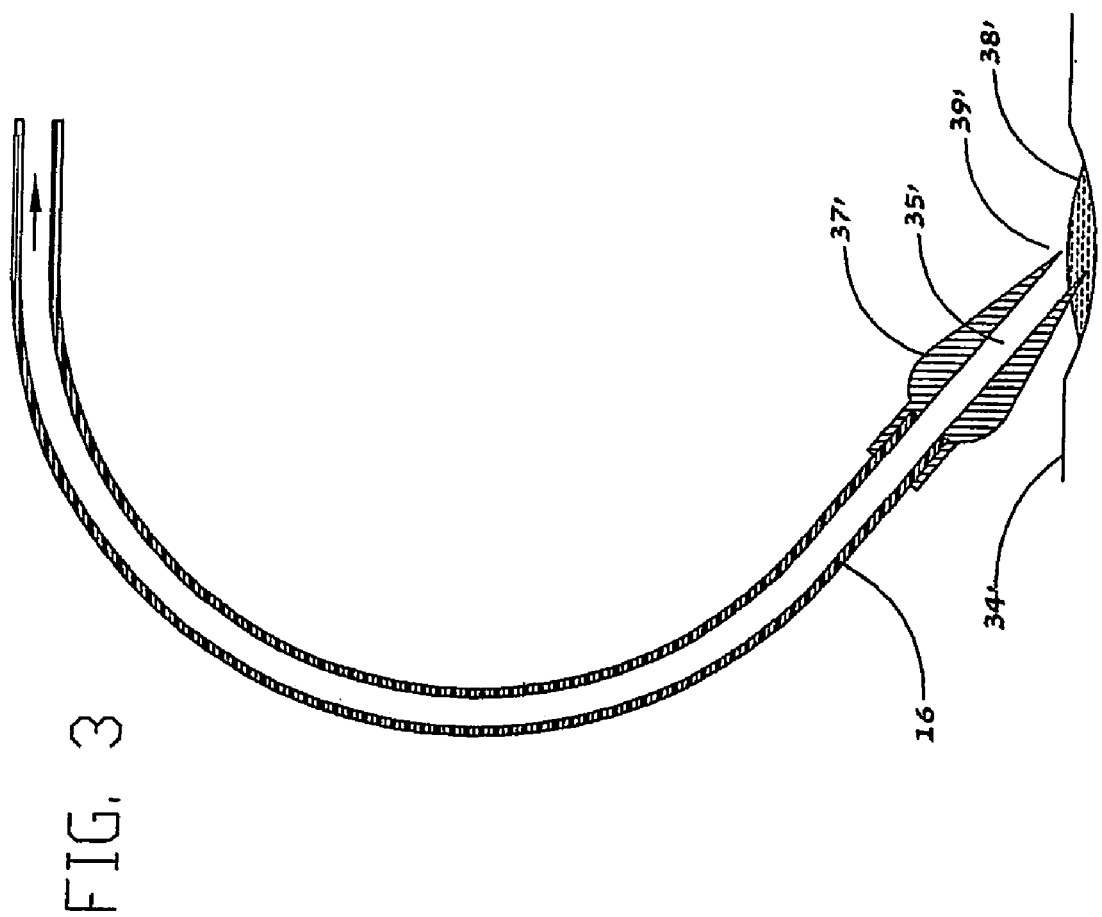
FIG. 3 is a schematic illustration in fragmented cross-sectional side view of an alternative suction head to that illustrated in FIGS. 1 and 2.

In one variation of the suction head, illustrated in FIG. 3, the free end or tip 37' of the conduit 16 (or 116 with respect to the second embodiment) comprises an inlet opening 35' that may be partially submerged in waste fluids 38' that it is desired to remove from target area 34', allowing a part 39' of the opening 35' to act as a venting orifice. This part 39' may function in a similar manner to the bleeding orifice 35 of the first embodiment, mutatis mutandis, but may change in size in response to changes in the relative positioning of the tip 37' with respect to the target 34'.

In the method claims that follow, alphanumeric characters and Roman numerals used to designate claim steps are provided for convenience only and do not imply any particular order of performing the steps.

It should be noted that the word "comprising" as used throughout the appended claims is to be interpreted to mean "including but not limited to".

While there has been shown and disclosed example embodiments in accordance with the invention, it will be appreciated that many changes may be made therein without departing from the spirit of the invention.

The invention claimed is:

1. A pump system, comprising:
   a head adapted for being in fluid communication with a target volume;
   a waste container defining a collection volume for collection of materials that may be drained from said target volume; and
   a pump apparatus comprising a powered pump drive and a pump head, in operation said pump apparatus being configured for enabling said pump drive to drive said pump head via a non-mechanical coupling arrangement, the pump head being in fluid communication with said head and with said waste container,
   wherein said non-mechanical coupling arrangement comprises a pneumatic coupling arrangement,
   wherein said pump apparatus comprises an actuation chamber that at least during operation of said system, is substantially air-tight and comprises a control volume of air that pneumatically couples the pump drive with the pump head, enabling said pump drive to drive said pump head,
   wherein said pump head is releasably coupled mechanically to said pump drive,
   wherein said actuation chamber comprises a first part, comprised in said pump head, and a second part, comprised in said pump drive, wherein said first part and said second part are configured for being reversibly sealably engaged with one another to define said control volume, when said pump head is coupled mechanically to said pump drive,
   wherein said pump head comprises a pump member in the form of a diaphragm, and said pump drive comprises a reciprocation drive for driving a reciprocating diaphragm member, said diaphragm member being in fluid communication with said actuation chamber only via a first surface thereof during operation of said system, and wherein said pump member and said diaphragm member are in mutually facing relationship in said actuation chamber.

2. A pump system according to claim 1, wherein said pump head comprises a pumping chamber and said pump member defining part of said pumping chamber, a pump inlet port and a pump outlet port, wherein said pump member is reciprocable via pneumatic coupling with said pump drive, to induce said working pressure in said pump system.

3. A pump system according to claim 2, wherein:
   said pump member constitutes a fluid barrier member substantially preventing fluid communication between any one of said suction head and said waste container, and said pump drive, via said drive head, and wherein
   said pump member is in fluid communication with said actuation chamber only via a first surface thereof, and wherein said first surface of said pump member is on an outside of said pumping chamber.

4. A pump system according claim 2, wherein said reciprocating diaphragm member and said pump member are pneumatically coupled one with the other via said actuation chamber at least when said system is in operation.

5. A pump system according to claim 2, comprising at least one of the following configurations:
   wherein said pump apparatus comprises a coupling interface for reversibly mechanically coupling said pump head with respect to said drive unit, and wherein said pump apparatus is configured for defining said actuation chamber responsive to said coupling interface being mechanically coupled to said pump head with respect to said drive unit, and
   wherein a part of said pump head is integral with said waste container, wherein said pump member is facing a direction generally away from said collection volume, and wherein said pump inlet port is at least partially within said collection volume.

6. A pump system according to claim 2, wherein a part of said pump head is accommodated in said waste container, wherein said pump member is facing a direction generally away from said collection volume, and wherein said pump inlet port is at least partially within said collection volume.

7. A pump system according to claim 6, comprising one or another of the following configurations:
   wherein said pump inlet port is in fluid communication with said head via a conduit, said pump outlet port is in fluid communication with said collection volume, and
   wherein said pump inlet port is in fluid communication with said head via said collection volume, and said pump outlet port is vented to said external ambient air.

8. A pump system according to claim 1, further comprising;
   a venting arrangement adapted for providing, at least during operation of said system, substantially permanent fluid communication between said suction head and said external environment, such as to enable said working pressure to be maintained at the head while enabling a desired flow rate of ambient air into the suction head via said venting arrangement, and wherein said venting arrangement optionally comprises at least one bleeding orifice comprising an effective flow area compatible with providing said desired flow rate.

9. A pump system according to claim 1, wherein said pump head, waste container and head are configured for being disposable.

10. A pump system according to claim 1, wherein said target volume is a medical target volume associated with a wound, burn or the like, and said head comprises an enclosure sealable to a perimeter of the wound burn or the like, respectively, so as to define a confined volume comprising said target volume.

11. A pump system according to claim 1, further comprising a non fluid invasive control system for monitoring said working pressure, said control system comprising at least one working parameter sensor for monitoring a working parameter of said powered pump drive and a comparator unit for comparing monitored data corresponding to said working parameter with threshold data, wherein the or each said working parameter is directly related to a magnitude of said working pressure provided by said pump apparatus.

12. A pump system according to claim 11, wherein said control system is configured for at least one of the following:
   calculating an estimated working pressure level based on monitored data corresponding to said working parameter; and
   monitoring a pressure of said control volume and comparing said estimated working pressure with said monitored pressure, and for optionally correcting said monitored data according to a difference determined between said estimated working pressure and said monitored pressure.

13. A pump system according to claim 1, further comprising a non fluid invasive monitoring system, with respect to fluids to be sucked via said system, for monitoring said working pressure, said monitoring system comprising at least one pressure sensor in fluid communication with said control volume and configured for monitoring a pressure thereof.

14. A pump system according to claim 11, wherein said monitoring system comprises at least one of: a suitable alarm configured for being activated when a magnitude of said monitored data exceeds or is below a magnitude of said threshold data; and a display for displaying said monitored data in any suitable manner.

15. A pump system comprising:
a pump apparatus comprising a powered pump drive and a pump head, in operation said pump apparatus being configured for enabling said pump drive to drive said pump head via a pneumatic coupling arrangement, the pump head being in fluid communication with said head,
wherein said pump apparatus comprises an actuation chamber that at least during operation of said system, is substantially air-tight and comprises a control volume of air that pneumatically couples the pump drive with the pump head, enabling said pump drive to drive said pump head,
wherein said pump head is releasably coupled mechanically to said pump drive,
wherein said actuation chamber comprises a first part, comprised in said pump head, and a second part, comprised in said pump drive, wherein said first part and said second part are configured for being reversibly sealably engaged with one another to define said control volume, when said pump head is coupled mechanically to said pump drive; and
wherein said pump head comprises a pump member in the form of a diaphragm, and said pump drive comprises a reciprocation drive for driving a reciprocating diaphragm member, said diaphragm member being in fluid communication with said actuation chamber only via a first surface thereof during operation of said system,
and further comprising at least one pressure sensor in fluid communication with said control volume and configured for monitoring a pressure thereof, and wherein said pump member and said diaphragm member are in mutually facing relationship in said actuation chamber.

16. A kit for use with a pump system for suctioning fluids from a target volume, comprising:
a pump head adapted for releasable operative coupling to a powered pump drive unit, said pump head comprising a pump inlet and a pump outlet for enabling working fluid to be pumped through the pump during operation thereof;

wherein said pump head is configured for being driven by said pump drive via a non-mechanical coupling arrangement,
wherein said non-mechanical coupling arrangement comprises a pneumatic coupling arrangement, wherein said pneumatic coupling arrangement comprises an actuation chamber that is formed when said pump head is coupled with said powered pump such that at least during operation of said system, said actuation chamber is substantially air-tight and comprises a control volume of air that pneumatically couples the pump drive with the pump head, enabling said pump drive to drive said pump head, and wherein optionally said actuation chamber comprises a first part, comprised in said pump head, and a second part, comprised in said pump drive, wherein said first part and said second part are configured for being reversibly sealably engaged with one another to define said control volume, at least when said pump system is in operation,
wherein said pump head comprises a pump member in the form of a diaphragm, and said pump drive comprises a reciprocation drive for driving a reciprocating diaphragm member, said diaphragm member being in fluid communication with said actuation chamber only via a first surface thereof during operation of said pump system, and wherein said pump member and said diaphragm member are in mutually facing relationship in said actuation chamber.

17. A method for indirectly monitoring a working pressure generated by a pump apparatus, said pump apparatus comprising a pump head comprising a pump member in the form of a diaphragm pneumatically coupled to a reciprocable diaphragm member of a powered pump drive unit via an actuation chamber comprising a control volume, and wherein said pump member and said diaphragm member are in mutually facing relationship in said actuation chamber, and further comprising monitoring directly a pressure of said control volume.

18. A pump system according to claim 1, further comprising an arrangement adapted for providing, at least during operation of said system, substantially permanent fluid communication between said head and an irrigation source, such as to enable irrigation of said target volume with a desired irrigation material.

* * * * *